United States Patent [19]

Lapoiriere et al.

[11] Patent Number: 5,077,058

[45] Date of Patent: Dec. 31, 1991

[54] ONE STEP PROCESS FOR PREPARING CROSS-LINKED POLY-$\beta$-ALANINE MICROSPHERES FROM ACRYLAMIDE AND A COPOLYMERISABLE POLYFUNCTIONAL COMPOUND

[75] Inventors: Claudine Lapoiriere, Le Perreux; Claude Mahieu, Paris; Christos Papantoniou, Montmorency, all of France

[73] Assignee: L'Oreal, Paris, France

[21] Appl. No.: 537,450

[22] Filed: Jun. 14, 1990

[30] Foreign Application Priority Data

Jun. 15, 1989 [FR] France .................................. 89 07946

[51] Int. Cl.$^5$ .......................... A61K 9/16; C08F 20/56
[52] U.S. Cl. ..................................... 424/501; 428/402; 526/303.1; 526/306; 526/307; 526/307.5; 526/203; 526/263; 526/281; 514/952
[58] Field of Search .......................... 424/489, 81, 501; 428/402; 526/303.1

[56] References Cited

U.S. PATENT DOCUMENTS 4,734,286  3/1988  Mahieu et al. ........................ 428/402
4,803,252  2/1989  Kida et al. ......................... 526/303.1

*Primary Examiner*—Thurman K. Page
*Assistant Examiner*—C. J. Webman
*Attorney, Agent, or Firm*—Cushman, Darby & Cushman

[57] ABSTRACT

A one-step process for preparing cross-linked poly-$\beta$-alanine as microspheres having narrow size distribution comprises polymerizing acrylamide with a polyfunctional compound copolymerizable with acrylamide (with the polyfunctional compound also acting as the cross-linking agent) in an organic solvent or a mixtured such solvents in the presence of an ionic polymerization initiator and a suspension agent. The resulting microspheres may be impregnated with a pharmaceutically or cosmetically active substance.

8 Claims, No Drawings

ONE STEP PROCESS FOR PREPARING CROSS-LINKED POLY-β-ALANINE MICROSPHERES FROM ACRYLAMIDE AND A COPOLYMERISABLE POLYFUNCTIONAL COMPOUND

This invention relates to a new process for preparing microspheres of cross-linked poly-β-alanine as well as to the thus produced microspheres which may be impregnated with a pharmaceutically or cosmetically active substance.

Cross-linked poly-β-alanine is known and has been described notably in French patent N° 83,11609 (2,530,250) as indeed has its process of preparation.

According to the process of this patent, the cross-linked poly-β-alanine is obtained in two steps, the first consisting of polymerising acrylamide to obtain water soluble poly-β-alanine and the second consisting of cross-linking, in suspension in an organic solvent, an aqueous solution of poly-β-alanine using a cross-linking agent such as a dialdehyde e.g. glutaraldehyde.

The cross-linked poly-β-alanine spheres obtained by this process are then sieved to obtain microspheres having a certain homogeneity of size.

According to the process of this patent, the microspheres are formed during cross-linking and their size depends essentially on the nature and quantity of the suspension agent used.

This process, requiring two steps as well as a subsequent sieving operation, is particularly cumbersome to execute and this fact significantly influences the cost price of the cross-linked poly-β-alanine.

After various studies, it has now been found that a cross-linked poly-β-alanine having excellent properties and having additionally a narrow particle size distribution may be achieved using a process comprising one step only.

In fact, it has been observed that by using polyfunctional compounds copolymerisable with acrylamide as cross-linking agents, it is possible to obtain, under given polymerisation conditions, cross-linked poly-β-alanine microspheres entirely comparable, in terms of their properties, to those obtained in the process of French patent N° 83,11609 which uses a dialdehyde such as glutaraldehyde as the cross-linking agent.

This process is particularly interesting from an industrial point of view, not only because it allows obtainment of cross-linked poly-β-alanine in a single step, but also because the microspheres obtained possess a measure of homogeneity of size thus avoiding the otherwise indispensable sieving step noted in French Patent N° 83,11609.

The process according to the invention is essentially characterised by the fact that it consists of polymerising acrylamide with a polyfunctional compound copolymerisable with acrylamide, the polyfunctional compound acting as cross-linking agent, the polymerisation being conducted in an organic solvent or in a mixture of such solvents in the presence of an ionic polymerisation initiator and of a suspension agent.

The polyfunctional compounds copolymerisable with acrylamide used as cross-linking agent according to the process of the invention are preferably unsaturated polyfunctional compounds having acrylamide, methacrylamide, acrylic ester, vinyl or allyl functions.

According to a preferred embodiment of the invention, these unsaturated polyfunctional compounds preferably carry acrylamide or methacrylamide functions.

These include the following: 1,2-dihydroxyethylene bis-acrylamide, N-N'-(bis-acrylyl) cysteamine, dimethylene bis-acrylamide, hexamethylene bis-acrylamide, octamethylene bis-acrylamide, dodecamethylene bis-acrylamide, m-xylylene bis-acrylamide, butylidene bis-acrylamide, benzylidene bis-acrylamide, diacrylamido acetic acid, xylylidene tetra-acrylamide, N,N'-bis(acrylyl) piperazine and p-benzylidene camphor N,N'-acrylyl diaminomethane. p-benzylidene camphor N,N'-acrylyl diaminomethane is described in French Patent N° 85,12959 (2,586,693).

Studies which have been carried out using diverse types of such unsaturated polyfunctional compounds have shown that it is preferable to use bifunctional compounds.

Although reference is made above to certain preferred compounds, it goes without saying that the invention is not limited solely to their use but that other polyfunctional compounds copolymerisable with acrylamide may also be used particularly those including other functions such as, for example, epoxy functions.

The organic solvent of the process according to the invention may be tert-butanol or toluene but preferably a mixture of these two in a ratio from 1:24 to 10:1, (preferably from 1:6 to 6:1). It has been observed in this respect, in a wholly surprising way, that by using such a mixture of solvents in a ratio as given above, it is possible to obtain poly-β-alanine microspheres having a very low size spread.

Regarding now the actual size of the microspheres, this depends essentially on the ratio between tert-butanol and toluene but also on the ratio of solvent mixture to acrylamide and on the stirring speed.

Generally, the greater the proportion of tert-butanol compared to toluene, the smaller the diameter of the resulting microspheres.

The anionic polymerisation initiator is preferably sodium or potassium tert-butylate taken in a proportion of from about 0.1 to about 2 mole % referred to the acrylamide.

The suspension agent of the process according to the invention is preferably an octadecene-maleic anhydride copolymer and more particularly the copolymer sold under the name "PA 18" by GULF.

The amount of suspension agent lies generally between 0.1 and 2% by weight referred to the acrylamide. The polymerisation temperature is of the order of 60° C. to about 100° C. but preferably about 80° C.

The cross-linked poly-β-alanine microspheres produced by the process according to the invention find application particularly in the therapeutic domain. They may be applied to infected or uninfected wounds and act as absorbants thus facilitating natural healing.

The cross-linked poly-β-alanine microspheres may also serve as a support for certain active substances.

In order to introduce the active substances into the cross-linked poly-β-alanine microspheres, the active product is dissolved in a solvent or mixture of solvents having sufficient affinity for the cross-linked poly-β-alanine. Appropriate solvents include water, glycerol, ethanol, diethyleneglycol, propyleneglycol and their mixtures or mixtures of water and water-miscible organic solvents such as for example acetone.

When using a solvent to obtain poly-β-alanine microspheres charged with active product, it is possible to use the microspheres as they are or alternatively after elimination of the solvent used for their impregnation. This same solvent may also act as a swelling agent for the microspheres themselves if indeed they are susceptible to swelling in the solvent chosen.

When the cross-linked poly-β-alanine microspheres are used after solvent removal, the active product remains trapped, even after drying, in (or on) the microspheres. The swelling of the cross-linked poly-β-alanine by a solvent leads to microspheres in the form of a gel providing that the quantity of solvent does not surpass certain limits which differ according to the exact nature of the cross-linked poly-β-alanine microspheres.

Whether dry or not, microspheres charged with at least one active substance may be mixed with a pharmaceutical or cosmetic vehicle.

Active substances may include the following: humectants, sunscreens, anti-inflammatories, anti-fungal agents, antibiotics, antiacne agents, antipurigineous agents for the softening of fingernails, skin fortifying agents, hairdressing agents, astringents, vitamins, essential oils, collagen, etc . . .

There follows, for the purposes of non-limitative illustration, several examples of the process of preparing the cross-linked poly-β-alanine according to the invention and examples of impregnation of the resulting microspheres using various active substances.

EXAMPLE 1

300 g of toluene, 147 g of tert-butanol and 0.5 g of octadecene-maleic anhydride copolymer (sold under the name "PA-18" by GULF) are introduced into a 2 liter reactor equipped with a 500 rpm mechanical stirrer, a cooler, a nitrogen supply and a means of controlling the temperature.

After heating the resulting mixture to 70° C., 45 g of acrylamide and 5 g of butylidene bis-acrylamide in 50 g of toluene are added. Then the temperature is brought to 80° C. and held there for about 15 mins. Next, 1.12 g of potassium tert-butylate in 20 g of tert-butanol (obtained by refluxing the mixture for two hours) is added over 10 mins.

After stirring for 6 hours at 80° C., the temperature is allowed to fall to ambient whereafter the cross-linked poly-β-alanine microspheres are filtered. After washing with ethanol and with water, the cross-linked poly-β-alanine microspheres are dried by lyophilisation (yield : 40%). The cross-linked poly-β-alanine microspheres appear as a white powder with the microspheres having an average diameter of 6 μm determined by the image analysis technique using a "QUANTIMET 900" device from Cambridge Instruments Co.

EXAMPLE 2

300 g of toluene, 147 g of tert-butanol and 0.5 g of octadecene-maleic anhydride copolymer (sold under the name "PA 18" by GULF) are introduced into a 2 liter reactor equipped with a 500 rpm mechanical stirrer, a cooler, a nitrogen supply and a means of controlling the temperature.

After heating the resulting mixture to 70° C., 48.75 g of acrylamide and 1.25 g of dimethylene bis-acrylamide in 50 g of toluene are added. Then the temperature is brought up to and held at 80° C. for about 15 mins. Next, 1.12 g of potassium tert-butylate in 20 g of tert-butanol (obtained by refluxing the mixture for two hours) is added over 10 mins.

After stirring for 5 hours at 80° C., the temperature is allowed to fall to ambient whereafter the cross-linked poly-β-alanine microspheres are filtered. After washing with ethanol and with water, the cross-linked poly-β-alanine microspheres are dried by lyophilisation (weight obtained : 40.5g). The cross-linked poly-β-alanine microspheres appear as a white powder with the microspheres having an average diameter of 7 μm determined by the image analysis technique using a "QUANTIMET 900" device from Cambridge Instruments Co.

EXAMPLES OF APPLICATIONS

Example A 50 g of the cross-linked poly-β-alanine microspheres obtained in Ex. 1 are suspended in a solution of 44.5 g of benzoyl peroxide (75% by weight) in a mixture of 1125g of acetone and 375 cm$^3$ of water.

The suspension is then concentrated in a rotary evaporator under reduced pressure below 35° C. until a total weight of 262 g of suspension is achieved.

The benzoyl peroxide content of the suspension is then 9.1 % by weight.

Example B 10 g of the cross-linked poly-β-alanine microspheres of Ex. 2 are suspended in a solution of 2 g of benzyl nicotinate in a mixture of 40 cm$^3$ of water and 40 g of ethanol.

The suspension is stirred for 2 hours after which the ethanol is removed by rotary evaporation below 35° C. The microspheres are then dried by lyophilization.

Example C 15 mg of butylhydroxytoluene (antioxidant) are dissolved in 30 g of 1,2-propyleneglycol at 30° C. After cooling to ambient, 24 mg of retinoic acid are added to the resulting mixture in darkness and in an atmosphere of argon. The solution obtained is filtered using 0.2 μm "Millipore" filters. Then 5 g of the cross-linked poly-β-alanine microspheres of example 2 are suspended in this solution in a current of argon while shielded from the light.

Mixing is done with a spatula and after 2 hours of absorption a yellow powder is obtained. The retinoic acid is assayed by spectrophotometry (λ=358.8nm) after desorption of the active principle in dimethylsulphoxide.

theoretical concentration : 0.16%
actual concentration : 0.157%

Example D 4 g of the cross-linked poly-β-alanine microspheres of example 1 are introduced while stirring into a solution of 3 g of essential oils of the perfume "Loulou" by Cacharel diluted by 9 g of propyleneglycol at 50° C.

The perfumed, powdery gel obtained is packaged in flasks.

Example E 20 g of benzylidene-3-d,l-camphor is dissolved in a mixture made up of 230 g of ethanol and 110 cm$^3$ of water previously heated to 40° C. The solution is then filtered before introducing into it 20 g of the cross-linked poly-β-alanine microspheres of example 2. Thereafter the ethanol is removed at 40° C. under reduced pressure and then the water by lyophilization.

Example F 2 g of Minoxidil are dissolved at 30° C. in a mixture of 75 g of ethanol and 75 cm$^3$ of water. To this solution, 8 g of the cross-linked poly-$\beta$-alanine microspheres of example 2 are added. After stirring the mixture for one hour in the rotary evaporator, the solvent is evaporated until a gel is obtained. The gel is then frozen while being stirred and is afterwards lyophilized. The concentration was 11.6% measured by UV at 230 nm after suspension in ethanol.

We claim:

1. A process for preparing cross-linked poly-$\beta$-alanine in the form of microspheres having a narrow size distribution, said process comprising polymerizing acrylamide with a polyfunctional compound copolymerizable with acrylamide, said polyfunctional compound carrying acrylamide or methacrylamide functions and acting as a cross-linking agent, in an organic solvent selected from the group consisting of tert.butanol, toluene and mixtures thereof in the presence of an anionic polymerization initiator and a suspension agent.

2. The process of claim 1 wherein said organic solvent is a tert.butanol.toluene mixture in a ratio of 1:24 to 10:1.

3. The process of claim 1 wherein said organic solvent is a tert.butanol/toluene mixture in a ratio of 1:6 to 6:1.

4. The process of claim 1 wherein said anionic polymerization initiator is sodium or potassium tert.butylate present in an amount ranging from 0.1 to 2 mole percent referred to the acrylamide.

5. The process of claim 1 wherein said suspension agent is an actadecene-maleic anhydride copolymer.

6. The process of claim 1, wherein said polyfunctional compound copolymerizable with acrylamide is selected from the group consisting of
1,2-dihydroxyethylene bis-acrylamide,
N,N'-(bis-acrylyl) cysteamine,
dimethylene bis-acrylamide,
hexamethylene bis-acrylamide,
octamethylene bis-acrylamide,
dodecamethylene bis-acrylamide,
m-xylylene bis-acrylamide,
butylidene bis-acrylamide,
benzylidene bis-acrylamide,
diacrylamido acetic acid,
xylylidene tetra-acrylamide,
N,N'-bis-(acrylyl) piperazine and
p-benzylidene camphor-N,N'-acrylyl diaminomethane.

7. Microspheres of cross-linked poly-$\beta$-alanine obtained according to the process of claim 1.

8. The microspheres of claim 7 charged with at least one pharmaceutically or cosmetically active substance.

* * * * *